(12) United States Patent
Burk et al.

(10) Patent No.: US 9,487,805 B2
(45) Date of Patent: Nov. 8, 2016

(54) BETAINE ESTERS AND PROCESS FOR MAKING AND USING

(71) Applicant: Eastman Chemical Company, Kingsport, TN (US)

(72) Inventors: Christopher Harlan Burk, Gray, TN (US); Stephanie Kay Clendennen, Kingsport, TN (US); Neil Warren Boaz, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/844,072

(22) Filed: Sep. 3, 2015

(65) Prior Publication Data

US 2015/0376662 A1   Dec. 31, 2015

Related U.S. Application Data

(60) Division of application No. 14/067,149, filed on Oct. 30, 2013, now abandoned, which is a continuation-in-part of application No. 13/096,221, filed on Apr. 28, 2011, now abandoned.

(51) Int. Cl.
| | |
|---|---|
| *C12P 13/04* | (2006.01) |
| *C07C 229/12* | (2006.01) |
| *C07C 219/06* | (2006.01) |
| *C07C 219/08* | (2006.01) |
| *C11D 1/90* | (2006.01) |

(52) U.S. Cl.
CPC .............. *C12P 13/04* (2013.01); *C07C 219/06* (2013.01); *C07C 219/08* (2013.01); *C07C 229/12* (2013.01); *C11D 1/90* (2013.01)

(58) Field of Classification Search
CPC ... C12P 13/04; C07C 229/12; C07C 219/06; C07C 219/08
See application file for complete search history.

(56) References Cited

U.S. PATENT DOCUMENTS

| | | | | |
|---|---|---|---|---|
| 2,727,049 A | * | 12/1955 | Braconier | C11C 3/04 554/167 |
| 2,804,474 A | * | 8/1957 | Lew | C07C 227/26 560/171 |
| 3,360,550 A | | 12/1967 | Cowen | |
| 4,137,191 A | * | 1/1979 | Lohr | A61K 8/44 510/125 |
| 4,339,391 A | | 7/1982 | Hoffmann et al. | |
| 4,564,477 A | | 1/1986 | Takigawa et al. | |
| 5,032,457 A | | 7/1991 | Wallach | |
| 5,180,508 A | | 1/1993 | Birkhan et al. | |
| 5,523,433 A | | 6/1996 | Toney et al. | |
| 5,750,492 A | | 5/1998 | Contet et al. | |
| 6,521,589 B2 | | 2/2003 | Demeyere et al. | |
| 7,667,067 B1 | | 2/2010 | Clendennen et al. | |
| 2006/0116290 A1 | | 6/2006 | Heming et al. | |
| 2009/0054521 A1 | | 2/2009 | Herrwerth et al. | |
| 2012/0040395 A1 | | 2/2012 | Clendennen | |
| 2012/0277324 A1 | | 11/2012 | Burk et al. | |
| 2013/0177951 A1 | | 7/2013 | Burk et al. | |

FOREIGN PATENT DOCUMENTS

| | | | | |
|---|---|---|---|---|
| CN | 1196351 | * | 10/1998 | .......... C07C 227/14 |
| EP | 0 309 052 A2 | | 3/1989 | |
| EP | 0 924 272 A1 | | 6/1999 | |
| EP | 1 249 488 A1 | | 10/2002 | |
| EP | 1 892 236 A1 | | 2/2008 | |
| ES | 459005 | * | 4/1978 | |
| ES | 459005 A1 | | 4/1978 | |
| JP | 62-189460 | | 8/1987 | |
| JP | 5132865 A | | 5/1993 | |
| JP | 6067122 A | | 3/1994 | |
| JP | 7216741 A | | 8/1995 | |
| JP | 07-234545 A1 | | 9/1995 | |
| JP | 2002 114647 A | | 4/2002 | |
| WO | WO 2012/148739 A1 | | 11/2012 | |

OTHER PUBLICATIONS

ES 459005, Pascual, J.O., Procedure for operation of surface active nitrogen, 1978, English translation 2 pages.*
CN1196351, Yan Kegang, et al., Syntehsis and separation of trimethyl glycine (betaine), 1998, English translation 5 pages.*
Jitputti, J., et al., Transesterification of palm kernel oil and coconut oil by difference solid catalysts, 2006, Asian Journal on Enerby and Environment, 7(04), pp. 423-433.*
Anonymous, "Enzymatic Esterification of Alkanolamines with Fatty Acids," Research Disclosure, Mason Publications, Hampshire, GB, vol. 457, No. 8, May 1, 2002.
Beare-Rogers, J. et al., Pure Appl. Chem., 2001, vol. 73, pp. 685-686, 697 and 731-735.
Cao, Z. et al., "Reversibly Switching the Function of a Surface between Attacking and Defending Against Bacteria", Angewandte Chemie International Edition English, vol. 51, Mar. 2012, pp. 2602-2605.
Carr, L. R. et al., "Functionalizable and Nonfouling Zwitterionic Carboxybetaine Hydrogels with a Carboxybetaine Dimethacrylate Crosslinker", Biomaterials, Elsevier Science Publishers BV., Barking, GB, vol. 32, No. 4, Feb. 1, 2011, pp. 961-968.
Chattopadhyay, Amitabha and London, Erwin; "Fluorimetric Determination of Critical Micelle Concentration Avoiding Interference from Detergent Charge"; Analytical Biochemistry 139, pp. 408-412, Dec. 1983.

(Continued)

*Primary Examiner* — Yate K Cutliff
(74) *Attorney, Agent, or Firm* — Matthew W. Smith

(57) ABSTRACT

A variety of betaine esters, including dialkylaminoalkyl cocoate betaines and dialkylaminoalkyl hydrogenated cocoate betaines are disclosed. These betaines can be advantageously prepared in high yield and purity by a three-step transiterification chemoenzymatic process or a two-step direct esterficiation chemoenzymatic process. These betaine esters have excellent surfactant properties.

13 Claims, No Drawings

(56) References Cited

OTHER PUBLICATIONS

Cui, G. et al., "Synthesis of Betaine-type Amphoteric Surfactants Based on Natural Rosin", [Online], Chemical Abstracts Service, Columbus, OH, Database accession No. 2007:1314346, RN 1187195-88-5.
Gandhi, N. N., "Applications of Lipase", Journal of the American Oil Chemists' Society, Springer, Berlin, DE, vol. 74, No. 6, Jun. 1, 1997, pp. 621-634.
Huang, Wei et al., "Enzymatic Esterification between n-alcohol homologs and n-caprylic acid in non-aqueous medium under microwave irradiation", Journal of Melecular Catalysis B: Enzymatic 25, 2005, pp. 113-116. XP002632069.
Jandke, Joachim and Spiteller, Gerhard; Liebigs Annalen der Chemie; 1988; 11; pp. 1057-1060.
Kitano, H. et al., "Image Printing on the Surface of Anti-biofouling Zwitterionic Poplymer Brishes by Ion Beam Irradiation", Macromolecular Bioscience, vol. 11, Apr. 8, 2011, pp. 557-564.
Miller, Carl et al.; "Characteristics of an Immobilized Lipase for the Commercial Synthesis of Esters"; Journal of the American Oil Chemists' Society, vol. 65, No. 6; Jun. 1988; pp. 927-931.
Shirato, Kazutaka et al., "Liquid fabric softening compositions containing polyoxyalkylenes and tertiary monoamine derivatives", Chemical Abstracts, Abstract No. 1995:890590.
Walsh, C. L. et al., "Synthesis and Characterization of Novel Zwitterionic Lipids with pH-responsive Biophysical Properties", Chemical Communication, vol. 48, Apr. 11, 2012, pp. 5575-5577.
Wang, L. et al., "Synthesis of Lauroylethyl Betaine Surfactant", [Online], Chemical Abstracts Service, Columbus, OH, Database accession No. 2011-1346379, RN 1338925-04-4.
Weng, W. et al., "A Water-soluble Amphoteric Copolymer: Synthesis and Its Dispersion Properties on Cement Particles", Journal of Applied Polymer Science, vol. 118, 2010, pp. 1313-1319.
Wengui, D. et al., "Synthesis of New Betaine-type Amphoteric Surfactants from Dehydroabietic Acid", [Online], Chemical Abstracts Service, Columbus, OH, Database accession No. 2005:1280259, RN 909405-44-3.
PCT International Search Report dated Jul. 11, 2012 for International Application No. PCT/US2012/033983.
International Search Report and Written Opinion for PCT/US2010/000472 dated Apr. 26, 2011.
PCT International Search Report and Written Opinion dated Oct. 29, 2013 for International Application No. PCT/US2013/000005.
Notification Concerning Transmittal of International Preliminary Report on Patentability and Written Opinion of International Searching Authority received in International Patent Application No. PCT/US2012/033983 dated Nov. 7, 2013.
Notification of Transmittal of the International Search Report and the Written Opinion of the International Searching Authority, or the Declaration date of mailing Jun. 20, 2014 received in International Patent Application No. PCT/US2013/067410.
Office Action notification date Mar. 6, 2014 received in co-pending U.S. Appl. No. 13/345,028.
Office Action notification date Jun. 11, 2015 received in co-pending U.S. Appl. No. 14/067,149.
English translation of ES 459005 pp. 1-8 (Apr. 1, 1978).

* cited by examiner

BETAINE ESTERS AND PROCESS FOR MAKING AND USING

CROSS REFERENCE TO RELATED APPLICATIONS

This application is a divisional of U.S. patent application Ser. No. 14/067,149 filed Oct. 30, 2013, now U.S. Patent Publication Number 2014-0050687; which is a continuation-in-part of U.S. patent application Ser. No. 13/096,221, filed Apr. 28, 2011, now abandoned; which are incorporated herein by reference in their entirety.

FIELD OF THE INVENTION

This invention pertains to betaine esters and processes for the preparation and use thereof.

BACKGROUND OF THE INVENTION

There is an increasing industrial and societal need for the preparation of ingredients that reduce or eliminate organic solvents and irritants, employ reagents that are themselves biocompatible and that optimally use starting materials derived from a natural source or are "nature-equivalent." This is of urgent interest in consumer-facing industries such as personal and household care. One class of materials that might be approached in a "greener" manner is surfactants. In particular, there is a need for new betaines that are made in a more environmentally-friendly manner. Betaines are zwitterionic surfactants used in the personal care, household care, and other industries. They are classified as specialty co-surfactants that complement the performance of the primary surfactants. These co-surfactants also increase the mildness of the formulation by reducing irritation associated with purely ionic surfactants.

Betaines are commonly produced by a multi-step process based on coconut or palm kernel oil. For example, one process for the preparation of a prototypical betaine, fatty acid amidopropyl betaine, involves the amidation of fatty acids with 3-dimethylaminopropylamine (DMAPA) at high temperatures (150-175° C.). The intermediate fatty amino-amide is then reacted with sodium chloroacetate to afford the final product. The amidation requires high temperatures for conversion and distillation to remove unreacted starting materials. These high reaction temperatures can generate by-products and impart color to the products, requiring additional steps to remove the by-products and the color. DMAPA is also a known sensitizer and is found in trace quantities in the final formulation. Thus, betaines prepared under mild conditions without the use of DMAPA would be of great interest.

It would be highly desirable for the production of the betaines to occur under mild conditions and in high yield. Such a process would take place at lower temperatures, with fewer processing steps and by-products and it would lessen environmental impacts. These objectives can be met, for example, by the transesterification process disclosed below, beginning with the first step of converting the fatty acid to its methyl ester. It would further be highly desirable for the production of the betaines to occur directly from the fatty acids, avoiding a process step and eliminating the use of an alcohol such as methanol and its required recycle.

BRIEF SUMMARY OF THE INVENTION

A first embodiment of the present invention concerns a compound represented by the general formula 1:

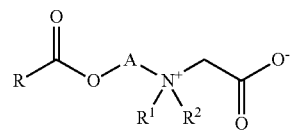

1 wherein R is selected from the group consisting of $C_5$-$C_{17}$ alkyl and mixtures thereof;

$R^1$ is methyl and $R^2$ is selected from the group consisting of $C_1$-$C_5$ alkyl; and A is selected from the group consisting of $C_3$-$C_{10}$ alkylene and $C_3$-$C_{10}$ alkenylene.

Another embodiment concerns a surfactant comprising the compound described above.

Yet another embodiment concerns a formulated product comprising the compound described above.

Still another embodiment concerns a transesterification process for the preparation of betaine, represented by the general formula 1,

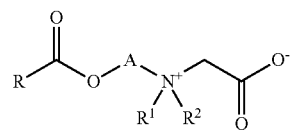

1 comprising:

a) producing an ester of formula 2:

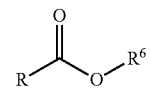

2 wherein R is selected from the group consisting of $C_5$-$C_{17}$ alkyl, $C_5$-$C_{17}$ alkenyl, $C_5$-$C_{17}$ dienyl, $C_5$-$C_{17}$ trienyl, and mixtures thereof, and $R^6$ is selected from the group consisting of $C_1$-$C_6$ alkyl;

b) reacting a dialkylamino alcohol 3:

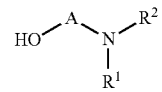

3 with ester 2 in the presence of an enzyme to form an intermediate 4:

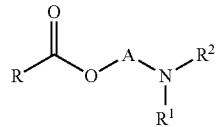

wherein $R^1$ is methyl and $R^2$ is selected from the group consisting of $C_1$-$C_5$ alkyl;

A is selected from the group consisting of $C_3$-$C_{10}$ alkylene and $C_3$-$C_{10}$ alkenylene, and c) reacting intermediate 4 with sodium chloroacetate to produce a betaine.

Still another embodiment concerns a direct esterification process for the preparation of betaine, represented by the general formula 1,

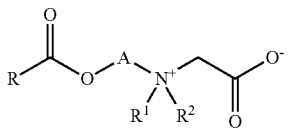

comprising:

a) reacting a carboxylic acid

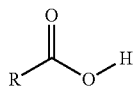

wherein R selected from the group consisting of $C_5$-$C_{17}$ alkyl, $C_5$-$C_{17}$ alkenyl, $C_5$-$C_{17}$ dienyl, $C_5$-$C_{17}$ trienyl, and mixtures thereof, and $R^6$ is a $C_1$-$C_6$ alkyl;

with a dialkylamino alcohol 3:

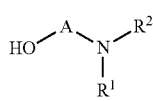

in the presence of an enzyme to form an intermediate 4:

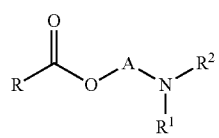

wherein $R^1$ is methyl and $R^2$ is selected from the group consisting of $C_1$-$C_5$ alkyl;

A is selected from the group consisting of $C_3$-$C_{10}$ alkylene and $C_3$-$C_{10}$ alkenylene; and b) reacting intermediate 4 with sodium chloroacetate to produce a betaine.

DETAILED DESCRIPTION

The present invention comprises a series of betaine compounds represented by the general formula 1:

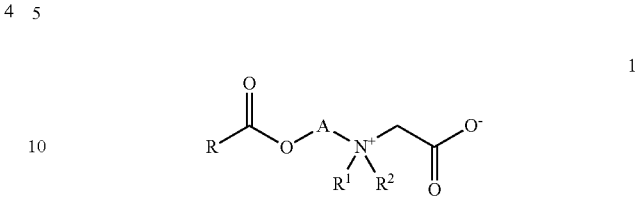

wherein R is selected from substituted and unsubstituted, branched- and straight-chain, saturated, unsaturated, and polyunsaturated $C_1$-$C_{22}$ hydrocarbyl, substituted and unsubstituted $C_3$-$C_8$ cycloalkyl, substituted and unsubstituted $C_6$-$C_{20}$ carbocyclic aryl, and substituted and unsubstituted $C_4$-$C_{20}$ heterocyclic wherein the heteroatoms are selected from sulfur, nitrogen, and oxygen, or mixtures thereof, and $R^1$ and $R^2$ may be the same or may be independently chosen from substituted or unsubstituted straight- or branched-chain $C_1$-$C_6$ alkyl, $C_2$-$C_6$ alkenyl, $C_4$-$C_6$ dienyl, and $C_3$-$C_8$ cycloalkyl groups wherein the branching and/or substitution of $R^1$ and $R^2$ may connect to form a ring, and A is selected from substituted and unsubstituted, branched- and straight-chain, saturated, unsaturated, and polyunsaturated $C_1$-$C_{10}$ divalent hydrocarbyl, substituted and unsubstituted $C_3$-$C_8$ cycloalkylene, substituted and unsubstituted $C_6$-$C_{10}$ carbocyclic arylene, and substituted and unsubstituted $C_4$-$C_{10}$ divalent heterocyclic wherein the heteroatoms are selected from sulfur, nitrogen, and oxygen.

According to an embodiment, the betaine compounds are denoted by structure 1 wherein R is selected from substituted and unsubstituted, branched- and straight-chain saturated $C_1$-$C_{22}$, $C_5$-$C_{17}$, $C_9$-$C_{17}$, and $C_5$-$C_{18}$ alkyl, substituted and unsubstituted, branched- and straight-chain $C_2$-$C_{22}$, $C_5$-$C_{17}$, $C_9$-$C_{17}$, and $C_5$-$C_{18}$ alkenyl, substituted and unsubstituted, branched- and straight-chain $C_4$-$C_{22}$, $C_5$-$C_{17}$, $C_9$-$C_{17}$, and $C_5$-$C_{18}$ dienyl, substituted and unsubstituted, branched- and straight-chain $C_6$-$C_{22}$, $C_5$-$C_{17}$, $C_9$-$C_{17}$, and $C_5$-$C_{18}$ trienyl, substituted and unsubstituted $C_3$-$C_8$ cycloalkyl, substituted and unsubstituted $C_6$-$C_{20}$ carbocyclic aryl, substituted and unsubstituted $C_4$-$C_{20}$ heteroaryl, $R^1$ and $R^2$ are selected from straight or branched chain $C_1$-$C_6$ and $C_1$-$C_5$ alkyl, $C_2$-$C_6$ alkenyl or $C_4$-$C_6$ dienyl, and A is selected from branched and straight chain $C_1$-$C_8$, $C_3$-$C_{10}$, and $C_3$-$C_8$, alkylene, branched- and straight-chain $C_2$-$C_8$, $C_3$-$C_{10}$, and $C_3$-$C_8$ alkenylene, substituted and unsubstituted $C_3$-$C_8$ cycloalkylene, substituted and unsubstituted $C_6$-$C_{10}$ carbocyclic arylene, substituted and unsubstituted $C_4$-$C_{12}$ divalent heterocyclic, or mixtures thereof.

The saturated, unsaturated, and polyunsaturated alkyl groups which may be represented by R may be straight- or branched-chain hydrocarbon radicals containing up to about 22 carbon atoms and may be substituted, for example, with one to five groups selected from $C_1$-$C_6$-alkoxy, carboxyl, amino, $C_2$-$C_{16}$ aminocarbonyl, $C_2$-$C_{16}$ amido, cyano, $C_2$-$C_7$-alkoxycarbonyl, $C_2$-$C_7$-alkanoyloxy, hydroxy, aryl, heteroaryl, thiol, thioether, $C_2$-$C_{10}$ dialkylamino, $C_3$-$C_{15}$ trialkylammonium and halogen. The terms "$C_1$-$C_6$-alkoxy", "$C_2$-$C_7$-alkoxycarbonyl", and "$C_2$-$C_7$-alkanoyloxy" are used to denote radicals corresponding to the structures —$OR^3$, —$CO_2R^3$, and —$OCOR^3$, respectively, wherein $R^3$ is $C_1$-$C_6$-alkyl or substituted $C_1$-$C_6$-alkyl. The terms "$C_2$-$C_{16}$ aminocarbonyl" and "$C_2$-$C_{16}$ amido" are used to denote radicals corresponding to the structures —$NHCOR^4$, —CONHR$^4$, respectively, wherein R$^4$ is C$_1$-C$_{15}$-alkyl or substituted C$_1$-C$_{15}$-alkyl. The term "C$_3$-C$_8$-cycloalkyl" is used to denote a saturated, carbocyclic hydrocarbon radical having three to eight carbon atoms.

The alkyl, alkenyl and dienyl groups which may be represented by R$^1$ and R$^2$ may be straight- or branched-chain hydrocarbon radicals containing up to about 6 carbon atoms and may be substituted, for example, with one to three groups selected from C$_1$-C$_6$-alkoxy, carboxyl, amino, C$_2$-C$_{16}$ aminocarbonyl, C$_2$-C$_{16}$ amido, cyano, C$_2$-C$_7$-alkoxycarbonyl, C$_2$-C$_7$-alkanoyloxy, hydroxy, aryl, heteroaryl, thiol, thioether, C$_2$-C$_{10}$ dialkylamino, C$_3$-C$_{15}$ trialkylammonium and halogen. The terms "C$_1$-C$_6$-alkoxy", "C$_2$-C$_7$-alkoxycarbonyl", and "C$_2$-C$_7$-alkanoyloxy" are used to denote radicals corresponding to the structures —OR$^3$, —CO$_2$R$^3$, and —OCOR$^3$, respectively, wherein R$^3$ is C$_1$-C$_6$-alkyl or substituted C$_1$-C$_6$-alkyl. The terms "C$_2$-C$_{16}$ aminocarbonyl" and "C$_2$-C$_{16}$ amido" are used to denote radicals corresponding to the structures —NHCOR$^4$, —CONHR$^4$, respectively, wherein R$^4$ is C$_1$-C$_{15}$-alkyl or substituted C$_1$-C$_{15}$-alkyl. The term "C$_3$-C$_8$-cycloalkyl" is used to denote a saturated, carbocyclic hydrocarbon radical having three to eight carbon atoms.

The divalent hydrocarbyl radicals which may be represented by A may be straight- or branched-chain saturated, unsaturated, and polyunsaturated alkylene and cycloalkylene groups containing up to about 10 carbon atoms and may be substituted, for example, with one to five groups selected from C$_1$-C$_6$-alkoxy, carboxyl, amino, C$_2$-C$_{16}$ aminocarbonyl, C$_2$-C$_{16}$ amido, cyano, C$_2$-C$_7$-alkoxycarbonyl, C$_2$-C$_7$-alkanoyloxy, hydroxy, aryl, heteroaryl, thiol, thioether, C$_2$-C$_{10}$ dialkylamino, C$_3$-C$_{15}$ trialkylammonium and halogen. The terms "C$_1$-C$_6$-alkoxy", "C$_2$-C$_7$-alkoxycarbonyl", and "C$_2$-C$_7$-alkanoyloxy" are used to denote radicals corresponding to the structures —OR$^3$, —CO$_2$R$^3$, and —OCOR$^3$, respectively, wherein R$^3$ is C$_1$-C$_6$-alkyl or substituted C$_1$-C$_6$-alkyl. The terms "C$_2$-C$_{16}$ aminocarbonyl" and "C$_2$-C$_{16}$ amido" are used to denote radicals corresponding to the structures —NHCOR$^4$, —CONHR$^4$, respectively, wherein R$^4$ is C$_1$-C$_{15}$-alkyl or substituted C$_1$-C$_{15}$-alkyl.

The aryl groups which R may represent (or any aryl substituents) may include phenyl, naphthyl, or anthracenyl and phenyl, naphthyl, or anthracenyl substituted with one to five substituents selected from C$_1$-C$_6$-alkyl, substituted C$_1$-C$_6$-alkyl, C$_6$-C$_{10}$ aryl, substituted C$_6$-C$_{10}$ aryl, C$_1$-C$_6$-alkoxy, halogen, carboxy, cyano, C$_2$-C$_7$-alkanoyloxy, C$_1$-C$_6$-alkylthio, C$_1$-C$_8$-alkylsulfonyl, trifluoromethyl, hydroxy, C$_2$-C$_7$-alkoxycarbonyl, C$_2$-C$_7$-alkanoylamino and —OR$^5$, —S—R$^5$, —SO$_2$—R$^5$, —NHSO$_2$R$^5$ and —NHCO$_2$R$^5$, wherein R$^5$ is phenyl, naphthyl, or phenyl or naphthyl substituted with one to three groups selected from C$_1$-C$_6$-alkyl, C$_6$-C$_{10}$ aryl, C$_1$-C$_6$-alkoxy and halogen.

The arylene groups which A may represent may include phenylene, naphthylene, or anthracenylene and phenylene, naphthylene, or anthracenylene substituted with one to five substituents selected from C$_1$-C$_6$-alkyl, substituted C$_1$-C$_6$-alkyl, C$_6$-C$_{10}$ aryl, substituted C$_6$-C$_{10}$ aryl, C$_1$-C$_6$-alkoxy, halogen, carboxy, cyano, C$_2$-C$_7$-alkanoyloxy, C$_1$-C$_6$-alkylthio, C$_1$-C$_6$-alkylsulfonyl, trifluoromethyl, hydroxy, C$_2$-C$_7$-alkoxycarbonyl, C$_2$-C$_7$-alkanoylamino and —OR$^5$, —S—R$^5$, —SO$_2$—R$^5$, —NHSO$_2$R$^5$ and —NHCO$_2$R$^5$, wherein R$^5$ is phenyl, naphthyl, or phenyl or naphthyl substituted with one to three groups selected from C$_1$-C$_6$-alkyl, C$_6$-C$_{10}$ aryl, C$_1$-C$_6$-alkoxy and halogen.

The heterocyclic groups which R may represent (or any heteroaryl substituents) include 5- or 6-membered ring containing one to three heteroatoms selected from oxygen, sulfur and nitrogen. Examples of such heterocyclic groups are pyranyl, oxopyranyl, dihydropyranyl, oxodihydropyranyl, tetrahydropyranyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heterocyclic radicals may be substituted, for example, with up to three groups such as C$_1$-C$_6$-alkyl, C$_1$-C$_6$-alkoxy, substituted C$_1$-C$_6$-alkyl, halogen, C$_1$-C$_6$-alkylthio, aryl, arylthio, aryloxy, C$_2$-C$_7$-alkoxycarbonyl and C$_2$-C$_7$-alkanoylamino. The heterocyclic radicals also may be substituted with a fused ring system, e.g., a benzo or naphtho residue, which may be unsubstituted or substituted, for example, with up to three of the groups set forth in the preceding sentence.

The divalent heterocyclic groups which A may represent include 5- or 6-membered ring containing one to three heteroatoms selected from oxygen, sulfur and nitrogen. Examples of such heterocyclic groups are pyranyl, oxopyranyl, dihydropyranyl, oxodihydropyranyl, tetrahydropyranyl, thienyl, furyl, pyrrolyl, imidazolyl, pyrazolyl, thiazolyl, isothiazolyl, oxazolyl, isoxazolyl, triazolyl, thiadiazolyl, oxadiazolyl, tetrazolyl, pyridyl, pyrimidyl, benzoxazolyl, benzothiazolyl, benzimidazolyl, indolyl and the like. The heterocyclic radicals may be substituted, for example, with up to three groups such as C$_1$-C$_6$-alkyl, C$_1$-C$_6$-alkoxy, substituted C$_1$-C$_6$-alkyl, halogen, C$_1$-C$_6$-alkylthio, aryl, arylthio, aryloxy, C$_2$-C$_7$-alkoxycarbonyl and C$_2$-C$_7$-alkanoylamino. The heterocyclic radicals also may be substituted with a fused ring system, e.g., a benzo or naphtho residue, which may be unsubstituted or substituted, for example, with up to three of the groups set forth in the preceding sentence.

The term "halogen" is used to include fluorine, chlorine, bromine, and iodine.

Examples of the compounds of the invention include those represented by formula 1 wherein R is a mixture of C$_5$ to C$_{17}$ hydrocarbyl radicals (derived from coconut oil), R$^1$ and R$^2$ are methyl and A is 1,3-propylene. In another aspect R is a mixture of C$_9$ to C$_{17}$ hydrocarbyl radicals (derived from stripped coconut oil), R$^1$ and R$^2$ are methyl and A is 1,3-propylene.

In an embodiment, the compound of the invention includes a compound represented by the general formula 1 wherein R is selected from the group consisting of C$_5$-C$_{17}$ alkyl and mixtures thereof; R$^1$ is methyl and R$^2$ is selected from the group consisting of C$_1$-C$_5$ alkyl; and A is selected from the group consisting of C$_3$-C$_{10}$ alkylene and C$_3$-C$_{10}$ alkenylene. In one aspect A is selected from the group consisting of C$_3$-C$_8$ alkylene and C$_3$-C$_8$ alkenylene. In one aspect R$^2$ is methyl. In yet another aspect, R is selected from the group consisting of C$_5$-C$_{17}$ alkyl and mixtures thereof, R$^2$ is methyl, and A is 1,3-propylene.

Specific examples of our inventive compound include 3-dimethylaminopropyl hydrogenated cocoate (R is a mixture of C$_5$-C$_{17}$) betaine, 3-dimethylaminopropyl hydrogenated stripped cocoate (R is a mixture of C$_9$-C$_{17}$) betaine, 3-dimethylaminopropyl laurate betaine, 3-dimethylaminopropyl myristate betaine, and 3-dimethylaminopropyl palmitate betaine.

Another embodiment concerns a transesterification process for the preparation of betaines represented by general formula 1. The first step of the transesterification process is the production of esters of the general formula 2:

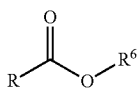

wherein R is defined above and $R^6$ may be $C_1$-$C_6$ straight or branched chain alkyl.

Short chain esters 2 can be produced by any practical method, including the solvolysis of non-hydrogenated or hydrogenated triglycerides in the presence of a lower alcohol and a base, acid or enzyme catalyst as is known in the art. Examples of lower alcohols include $C_1$-$C_4$ alcohols such as methanol, ethanol, 1-propanol, 2-propanol, 1-butanol, 2-butanol, and isobutanol. The short-chain esters 2 may contain from 0-20% of residual lower alcohol.

The second step of the transesterification process comprises the enzymatic reaction of a dialkylamino alcohol 3:

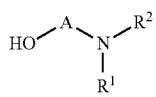

with ester 2 in the presence of an enzyme with or without methods for the removal of the alcohol by-product to form the desired intermediate 4, wherein R, $R^1$, $R^2$ and A are defined above.

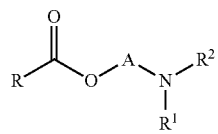

In one aspect of the transesterification process, R is selected from $C_5$-$C_{17}$ alkyl, $C_5$-$C_{17}$ alkenyl, $C_5$-$C_{17}$ dienyl, $C_5$-$C_{17}$ trienyl, and mixtures thereof; $R^6$ is a $C_1$-$C_6$ alkyl; $R^1$ is methyl and $R^2$ is selected from the group consisting of $C_1$-$C_5$ alkyl; and A is selected from $C_3$-$C_{10}$ alkylene and $C_3$-$C_{10}$ alkenylene. In another aspect, R is selected from $C_5$-$C_{17}$ alkyl and mixtures thereof; $R^1$ is methyl and $R^2$ is selected from $C_1$-$C_5$ alkyl, and A is selected from $C_3$-$C_8$ alkylene and $C_3$-$C_8$ alkenylene. In another aspect, the lower alcohol is a $C_1$-$C_4$ alcohol, $R^2$ is methyl, and A is selected from $C_3$-$C_8$ alkylene and $C_3$-$C_8$ alkenylene. In yet another aspect, the lower alcohol is selected from methanol, ethanol, 1-propanol, and 2-propanol, and A is 1,3-propylene.

The second step of the transesterification process is carried out without solvent or in an inert solvent chosen from cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof. In one aspect, no solvent is used. In another aspect, heptane is used as the solvent. In one aspect, the solvent forms an azeotrope with the $C_1$-$C_4$ alcohol facilitating removal of the alcohol from the reaction mixture and driving the reaction to higher conversions.

The second step of the transesterification process may be carried out at a temperature from about -100° C. to about the boiling point of the solvent, from about 20 to about 80° C., or from about 50 to about 70° C. The amount of alcohol 3 may be from about 0.85 to about 20 equivalents based on the ester 2, or can be from about 1 to about 10 equivalents, or even from about 1 to about 1.5 equivalents. The use of short chain alcohol esters of carboxylic acids is beneficial to the success of the enzymatic esterification of the amino alcohol.

The enzyme used in the second step of the transesterification process is chosen from a protease, a lipase, or an esterase. Moreover, lipases may be in the form of whole cells, isolated native enzymes, or immobilized on supports. Examples of these lipases include but are not limited to Lipase PS (from *Pseudomonas* sp), Lipase PS-C (from *Psuedomonas* sp immobilized on ceramic), Lipase PS-D (from *Pseudomonas* sp immobilized on diatomaceous earth), Lipoprime 50T, Lipozyme TL IM, Novozym 435 (*Candida antarctica* lipase B immobilized on acrylic resin) or *Candida antarctica* lipase B immobilized on a porous fluoropolymer support as described in US Patent Pub. 20120040395.

Removal of the alcohol byproducts can be done chemically via an alcohol absorbent (e.g., molecular sieves) or by physical removal of the alcohol. According to an embodiment, this by-product removal can be done by evaporation, either by purging the reaction mixture with an inert gas such as nitrogen, argon, or helium, or by performing the reaction at reduced pressures, or both, as these conditions can afford >98% conversion of ester 2 to intermediate 4. According to an embodiment, pressure for the reaction is from about 1 torr to about ambient pressure, or from about 50 torr to about ambient pressure. Any organic solvent that is included in this process may or may not be removed along with the alcohol. In one aspect, the organic solvent also functions to assist in removal of the alcohol byproduct by azeotropic distillation. Examples of dialkylamino alcohol 3 include dimethylaminoethanol and dimethylaminopropanol.

The third step of the transesterification process to generate the final product 1 comprises the reaction of intermediate 4 with sodium chloroacetate. The third step of the transesterification process can be carried out without solvent or in an inert solvent chosen from water, cyclic or acyclic alcohol solvents such as methanol, ethanol, 1-propanol, 2-propanol, 1-butanol, 2-butanol, isobutanol, ethylene glycol, 1,2-propanediol, or 1,3-propanediol, cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof.

The third step of transesterfication process may be carried out at a temperature of from about -100° C. to about the boiling point of the solvent, from about 25 to about 150° C., or from about 50 to about 100° C. The amount of sodium chloroacetate may be from about 0.75 to about 20 equivalents based on the amount of intermediate 4, from about 1 to about 10 equivalents, or from about 1 to about 1.5 equivalents. If included, a base is chosen from metal hydroxides, metal carbonates, or metal bicarbonates. According to an embodiment, bases can be sodium hydroxide, potassium hydroxide, sodium bicarbonate, and potassium bicarbonate. The amount of base can be from about 0 molar equivalents to about 1 molar equivalent based on intermediate or in an amount high enough to keep the reaction mixture basic, for example at about pH 8-9.

The intermediate 4 and the product 1 of the process may be isolated using methods known to those of skill in the art, e.g., extraction, filtration, or crystallization.

Another embodiment concerns a direct esterification process for the preparation of betaines represented by general formula 1. The first step of the esterification process comprises the reaction of a carboxylic acid

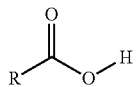

wherein R selected from $C_5$-$C_{17}$ alkyl, $C_5$-$C_{17}$ alkenyl, $C_5$-$C_{17}$ dienyl, $C_5$-$C_{17}$ trienyl, and mixtures thereof, with a dialkylamino alcohol 3:

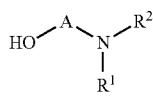

3 in the presence of an enzyme to form an intermediate 4:

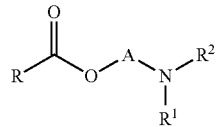

4 wherein $R^1$ is methyl and $R^2$ is selected from $C_1$-$C_5$ alkyl; and A is selected from $C_3$-$C_{10}$ alkylene and $C_3$-$C_{10}$ alkenylene. The second step of the direct esterification process comprises reacting intermediate 4 with sodium chloroacetate to produce a betaine.

In one aspect of the direct esterification process, R is selected from $C_5$-$C_{17}$ alkyl and mixtures thereof; $R^1$ is methyl and $R^2$ is selected from $C_1$-$C_5$ alkyl, and A is selected from $C_3$-$C_8$ alkylene and $C_3$-$C_8$ alkenylene. In another aspect, $R^2$ is methyl, and A is selected from $C_3$-$C_8$ alkylene and $C_3$-$C_8$ alkenylene. In yet another aspect, $R^2$ is methyl and A is 1,3-propylene.

The first step of the direct esterification process can be carried out without solvent or in an inert solvent chosen from cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof. In one aspect, no solvent is used. In one aspect, heptane is used as the solvent. In one aspect, the solvent serves as an agent coping agent with water facilitating removal of water from the reaction mixture and driving the reaction to higher conversions.

The first step of the direct esterification process may be carried out at a temperature from about −100° C. to about the boiling point of the solvent, from about 20 to about 80° C., or from about 50 to about 70° C. The amount of dialkylamino alcohol 3 may be from about 0.85 to about 20 equivalents based on the carboxylic acid, or can be from about 1 to about 10 equivalents, or even from about 1 to about 1.5 equivalents.

The enzyme used in the first step of the direct esterification process is chosen from a protease, a lipase, or an esterase. Moreover, lipases may be in the form of whole cells, isolated native enzymes, or immobilized on supports. Examples of these lipases include but are not limited to Lipase PS (from *Pseudomonas* sp), Lipase PS-C (from *Psuedomonas* sp immobilized on ceramic), Lipase PS-D (from *Pseudomonas* sp immobilized on diatomaceous earth), Lipoprime 50T, Lipozyme TL IM, Novozym 435 (*Candida antarctica* lipase B immobilized on acrylic resin) or *Candida antarctica* lipase B immobilized on a porous fluoropolymer support as described in US Patent Pub. 20120040395.

Removal of the water byproducts can be done chemically via a water absorbent (e.g., molecular sieves) or by physical removal of the water. According to an embodiment, this by-product removal can be done by evaporation, either by purging the reaction mixture with an inert gas such as nitrogen, argon, or helium, or by performing the reaction at reduced pressures, or both, as these conditions can afford >98% conversion of the carboxylic acid to intermediate 4. According to an embodiment, pressure for the reaction is from about 1 torr to about ambient pressure, or from about 50 torr to about ambient pressure. Any organic solvent that is included in this process may or may not be removed along with the water. In one aspect, the organic solvent also functions to assist in removal of the water byproduct by azeotropic distillation. Examples of dialkylamino alcohol 3 include dimethylaminopropanol.

The second step of the direct esterification process to generate the final product 1 comprises the reaction of intermediate 4 with sodium chloroacetate. The second step of the direct esterification process can be carried out without solvent or in an inert solvent chosen from water, cyclic or acyclic alcohol solvents such as methanol, ethanol, 1-propanol, 2-propanol, 1-butanol, 2-butanol, isobutanol, ethylene glycol, 1,2-propanediol, or 1,3-propanediol, cyclic or acyclic ether solvents such as diethyl ether, diisopropyl ether, tert-butyl methyl ether, or tetrahydrofuran, aromatic hydrocarbons such as benzene, toluene, or xylene, aliphatic or alicyclic saturated or unsaturated hydrocarbons such as hexane, heptane, cyclohexane, or limonene, halogenated hydrocarbons such as dichloromethane, dichloroethane, dibromoethane, tetrachloroethylene, or chlorobenzene, polar aprotic solvents such as acetonitrile, dimethyl formamide, or dimethyl sulfoxide, or mixtures thereof.

The second step of direct esterification process may be carried out at a temperature of from about −100° C. to about the boiling point of the solvent, from about 25 to about 150° C., or from about 50 to about 100° C. The amount of sodium chloroacetate may be from about 0.75 to about 20 equivalents based on the amount of intermediate 4, from about 1 to about 10 equivalents, or from about 1 to about 1.5 equivalents. If included, a base is chosen from metal hydroxides, metal carbonates, or metal bicarbonates. According to an embodiment, bases can be sodium hydroxide, potassium hydroxide, sodium bicarbonate, and potassium bicarbonate. The amount of base can be from about 0 molar equivalents to about 1 molar equivalent based on intermediate 4 or in an amount high enough to keep the reaction mixture basic, for example at about pH 8-9.

The intermediate 4 and the product 1 of the process may be isolated using methods known to those of skill in the art, e.g., extraction, filtration, or crystallization.

Another embodiment of the invention is the use of the betaine esters 1 as surfactants. The surfactant properties of the betaine esters 1 can be determined by a number of tests including an ASTM foam height test and a test for critical micelle concentration.

The Standard Test Method for Foaming Properties of Surface-Active Agents (ASTM 1173-07) was used to determine the foaming properties of the betaine esters 1 described herein. This method generates foam under low-agitation conditions and is generally used for moderate- and high-foam surfactants. This test gathers data on initial foam height and foam decay. Foam decay provides information on foam stability.

The apparatus for carrying out this test includes a jacketed column and a pipet. The jacketed column serves as a receiver, while the pipet delivers the surface-active solution. Solutions of each surface-active agent were prepared. The betaine solution to be tested was added to the receiver (50 mL) and to the pipet (200 mL). The pipet was positioned above the receiver and opened. As the solution fell and made contact with the solution in the receiver, foam was generated. When the pipet was empty, the time was noted and an initial foam height was recorded. The foam height was recorded each minute for five minutes. Exact size specifications for the glassware can be found in ASTM 1173-07.

Data from the foam height test can be found in Table 1. Examples 4-6, 8, 9, 11, 14, 16, 18, 20, and 22 are betaine esters, while Comparative Examples 2, 4, 6 and 8 are betaine amides for comparison. These compounds were prepared at 1 g/L and 10 g/L solutions. As the data in Table 1 indicate, solutions of the betaine esters generate large amounts of foam. Examples in which foam height does not decrease over time indicate good foam stability. Comparative Example 2 is a useful standard, in that this compound is used commercially as a betaine surfactant.

The critical micelle concentration (CMC) was also determined for each compound. The CMC is the concentration of surfactants above which micelles spontaneously form. CMC is an important characteristic of a surfactant. At surfactant concentrations below the CMC, surface tension varies widely with surfactant concentration. At concentrations above the CMC, surface tension remains fairly constant. A lower CMC indicates less surfactant is needed to saturate interfaces and form micelles. Typical CMC values for surface-active agents are less than 1 weight %.

The fluorimetric determination of CMC described by Chattopadhyay and London (*Analytical Biochemistry,* 139, 408-412, 1984) was used to obtain the critical micelle concentrations found in Table 2. This method employs the fluorescent dye 1,6-diphenyl-1,3,5-hexatriene (DPH) in a solution of the surface-active agent. The analysis is based on differences in fluorescence upon incorporation of the dye into the interior of the micelles. As the solution exceeds CMC, a large increase in fluorescence intensity is observed. This method has been found to be sensitive and reliable, and has been demonstrated on zwitterionic, anionic, cationic and uncharged surface-active agents.

TABLE 1

| | Foam height (cm) at time t (min) | | | | | | | | | | | |
|---|---|---|---|---|---|---|---|---|---|---|---|---|
| | 1 g/L (0.1 weight %) | | | | | | 10 g/L (1.0 weight %) | | | | | |
| | t = 0 | 1 | 2 | 3 | 4 | 5 | t = 0 | 1 | 2 | 3 | 4 | 5 |
| Example No. | | | | | | | | | | | | |
| 4 | 9.0 | 9.0 | 9.0 | 9.0 | 9.0 | 9.0 | 16.5 | 16.5 | 16.0 | 16.0 | 16.0 | 16.0 |
| 5 | 15.0 | 14.0 | 14.0 | 13.5 | 13.5 | 13.5 | 17.0 | 16.5 | 16.0 | 15.5 | 15.5 | 15.0 |
| 6 | 16.0 | 15.5 | 15.5 | 15.5 | 15.5 | 15.5 | 15.0 | 15.0 | 15.0 | 15.0 | 15.0 | 15.0 |
| 8 | 14.0 | 13.5 | 13.5 | 13.5 | 13.0 | 13.0 | 17.0 | 16.0 | 15.5 | 15.5 | 15.0 | 15.0 |
| 9 | 15.5 | 15.0 | 15.0 | 14.5 | 14.5 | 14.0 | 17.0 | 16.0 | 15.5 | 15.5 | 15.5 | 15.0 |
| 11 | 10.0 | 10.0 | 10.0 | 10.0 | 9.5 | 9.5 | 21.0 | 19.5 | 19.0 | 19.0 | 18.5 | 18.5 |
| 14 | 16.5 | 16.0 | 16.0 | 15.5 | 15.5 | 15.5 | 16.0 | 15.5 | 15.5 | 15.0 | 15.0 | 15.0 |
| 16 | 17.0 | 16.5 | 15.5 | 15.5 | 15.0 | 13.5 | 17.5 | 17.0 | 17.0 | 17.0 | 16.5 | 16.5 |
| 18 | 17.0 | 16.5 | 16.5 | 16.5 | 16.5 | 16.5 | 18.0 | 17.0 | 17.0 | 16.5 | 16.5 | 16.5 |
| 20 | 17.0 | 16.0 | 15.5 | 15.5 | 15.0 | 15.0 | 19.0 | 16.5 | 16.5 | 15.5 | 15.5 | 15.5 |
| 22 | 4.0 | 3.5 | 3.5 | 3.0 | 2.5 | 2.5 | ND | ND | ND | ND | ND | ND |
| Comparative example no. | | | | | | | | | | | | |
| 2 | 17.0 | 16.5 | 16.5 | 16.0 | 16.0 | 16.0 | 17.5 | 17.0 | 17.0 | 16.5 | 16.5 | 16.5 |
| 4 | 15.5 | 15.5 | 15.5 | 15.5 | 15.5 | 15.5 | 16.5 | 16.0 | 15.5 | 15.5 | 15.5 | 15.5 |
| 6 | 16.5 | 16.0 | 15.5 | 15.5 | 15.5 | 15.5 | 17.5 | 17.0 | 16.5 | 16.5 | 16.0 | 15.5 |
| 8 | 16.0 | 15.0 | 15.0 | 14.0 | 12.0 | 5.0 | 17.0 | 15.5 | 14.0 | 13.0 | 7.0 | 5.0 |

TABLE 2

| Example No. | CMC (weight %) |
|---|---|
| 4 | 0.0050 |
| 5 | 0.0053 |
| 6 | 0.0007 |
| 8 | 0.0045 |
| 9 | 0.0023 |
| 11 | 0.0004 |
| 14 | 0.0042 |
| 16 | 0.0026 |
| 18 | 0.0092 |
| 20 | 0.0020 |
| 22 | 0.0006 |
| Comparative Example No. | |
| 2 | 0.0029 |
| 4 | 0.0041 |
| 6 | 0.0025 |
| 8 | 0.0027 |

The data in Table 2 indicate that very low concentrations of the betaine esters are needed to reach CMC. Again, Examples 4-6, 8, 9, 11, 14, 16, 18, 20, and 22 are betaine esters, while Comparative Examples 2, 4, 6 and 8 are betaine amides for comparison. As with foam height, all of these compounds appear similar. These values fall in the range of being useful as surface-active agents. As noted above, Comparative Example 2 is used commercially as a betaine surfactant and provides a reference point by which to compare values for the betaine esters of general formula 1.

The betaine esters are molecules possessing both hydrophilic and hydrophobic regions, making them useful as surfactants in a number of formulated product applications, including personal care products such as skin care, hair care or other cosmetic products, household and industrial surface cleaners, disinfectants, metal working, rust inhibitors, lubricants, agrochemicals, dye dispersions, oil field additives, and oil dispersants. Betaines can also be used as emulsifiers and thickening agents in emulsions. Betaines are often formulated into products as secondary surface-active agents. Although a primary use is as humectants and foaming agents, betaines are also used for their anti-static and viscosity-controlling properties.

Such product formulations can contain from about 0.001 weight % to about 20 weight %, from about 0.01 weight % to about 15 weight %, or even from about 0.1 weight % to about 10 weight % of the betaine esters.

Product formulations of the invention may include other surfactants in addition to the betaine esters. These surfactants can include anionic surfactants (such as alcohol ether sulfates, linear alkylbenzene sulfonates, acyl isethionates), cationic surfactants (such as quaternary ammonium salts, fatty amine oxides, and ester quats), and non-ionic surfactants (such as alky polyglycosides, alcohol ethoxylates, and fatty alcanol amides). Such ingredients are known to those of skill in the art.

The cosmetic, skin, and hair care compositions of the invention may also contain other skin conditioning ingredients or cosmetically acceptable carriers in addition to the betaine esters.

Such formulations may also contain skin care ingredients/carriers such as retinol, retinyl esters, tetronic acid, tetronic acid derivatives, hydroquinone, kojic acid, gallic acid, arbutin, α-hydroxy acids, niacinamide, pyridoxine, ascorbic acid, vitamin E and derivatives, aloe, salicylic acid, benzoyl peroxide, witch hazel, caffeine, zinc pyrithione, and fatty acid esters of ascorbic acid. Such other ingredients are known to those of skill in the art.

Other ingredients that may be included in these formulations include conditioning agents (such as polyquaterniums and panthenol), pearlizing agents (such as glycol distearate, distearyl ether, and mica), UV filters (such as octocrylene, octyl methoxycinnamate, benzophenone-4, titanium dioxide, and zinc oxide), exfoliation additives (such as apricot seeds, walnut shells, polymer beads, and pumice), silicones (such as dimethicone cyclomethicone, and amodimethicone), moisturizing agents (such as petrolatum, sunflower oil, fatty alcohols, and shea butter), foam stabilizers (such as cocamide MEA and cocamide DEA), anti-bacterial agents such as triclosan, humectants such as glycerin, thickening agents (such as guar, sodium chloride, and carbomer), hair and skin damage repair agents (such as proteins, hydrolyzed proteins, and hydrolyzed collagen), and foam boosters such as cocamide MIPA. Such other ingredients are known to those of skill in the art.

Many preparations are known in the art, and include formulations containing acceptable carriers such as water, oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like. These same general ingredients can be formulated into liquids (such as liquid soaps, shampoos, or body washes), creams, lotions, gels, or into solid sticks by utilization of different proportions of the ingredients and/or by inclusion of thickening agents such as gums or other forms of hydrophilic colloids.

EXAMPLES

The processes and compounds provided by the present invention are further illustrated by the following examples.

Example 1

Preparation of Methyl Cocoate

To a jar was added potassium hydroxide (1 g) and methanol (25 g). The solution was stirred for 1 hour. To a separate jar was added coconut oil (100 g). The solid was heated to a melt and the KOH/MeOH solution was added and the mixture was stirred overnight. The mixture was transferred to a separatory funnel and allowed to separate. The bottom (glycerol) layer was removed. The top layer was filtered to afford a pale yellow oil (100 g). $^1$H NMR (300 MHz, CDCl$_3$) δ 3.65 (s, 3H), 2.28 (t, 2H), 1.60 (m, 2H), 1.24 (s, 16H), 0.86 (t, 3H).

Example 2

Preparation of Ethyl Cocoate

To a jar was added potassium hydroxide (2 g) and ethanol (72 g). The solution was stirred for 1 hour. To a separate jar was added coconut oil (200 g). The solid was heated to a melt and the KOH/EtOH solution was added and the mixture was stirred overnight. The mixture was transferred to a separatory funnel and allowed to separate. The bottom (glycerol) layer was removed. The top layer was filtered to afford a pale yellow oil (227 g). $^1$H NMR (300 MHz, CDCl$_3$) δ 4.09 (t, 3H), 3.68 (q, 2H), 2.27 (t, 2H), 1.60 (m, 2H), 1.24 (s, 16H), 0.86 (t, 3H).

Example 3

Preparation of Dimethylaminoethyl Cocoate

To a 50 mL conical bottom plastic vial was added ethyl cocoate (10 g, 38.5 mmol), dimethylaminoethanol (5.09 g, 57.7 mmol, 1.5 eq) and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale yellow oil (8 g) without further purification. $^1$H NMR (300 MHz, CDCl$_3$) δ 4.15 (t, 2H), 2.54 (t, 2H), 2.31 (t, 2H), 2.26 (s, 6H), 1.60 (m, 2H), 1.24 (s, 16H), 0.86 (t, 3H).

Example 4

Preparation of Dimethylaminoethyl Cocoate Betaine

To a 100 mL round bottom flask with a magnetic stir bar and a condenser was added dimethylaminoethyl cocoate (10 g, 35.3 mmol), sodium chloroacetate (4.11 g, 35.3 mmol, 1 eq) and water (32.9 g). The reaction mixture was heated at 98° C. for 8 hours. The pH was kept basic by the addition of 50% NaOH. When the reaction was complete, the mixture was neutralized with 1 M HCl and allowed to cool. The reaction mixture was filtered to afford the product as a 30% aqueous solution (43 g). $^1$H NMR (300 MHz, DMSO d-6) δ 3.89 (t, 2H), 3.78 (t, 2H), 3.66 (s, 2H), 3.17 (s, 6H), 2.27 (t, 2H), 1.51 (m, 2H), 1.23 (s, 16H), 0.85 (t, 3H).

Example 5

Preparation of Dimethylaminoethyl Cocoate Betaine

To a 100 mL round bottom flask with a magnetic stir bar and a condenser was added dimethylaminoethyl cocoate (10 g, 35.3 mmol), sodium chloroacetate (4.11 g, 35.3 mmol, 1 eq) and 1,3-propanediol (4.7 g). The reaction mixture was heated at 98° C. for 8 hours. When the reaction was complete by NMR, the mixture was allowed to cool. The mixture was filtered to afford the product as a viscous, 75% solution in 1,3-propanediol (14 g). $^1$H NMR (300 MHz, DMSO d-6) δ 3.89 (t, 2H), 3.78 (t, 2H), 3.66 (s, 2H), 3.17 (s, 6H), 2.27 (t, 2H), 1.51 (m, 2H), 1.23 (s, 16H), 0.85 (t, 3H).

Example 6

Preparation of Dimethylaminoethyl Cocoate Betaine

To a 100 mL round bottom flask with a magnetic stir bar and a condenser was added dimethylaminoethyl cocoate (10 g, 35.3 mmol), sodium chloroacetate (4.11 g, 35.3 mmol, 1 eq) and isopropanol (15 mL). The reaction mixture was heated at reflux for 8 hours. When the reaction was complete by NMR, the mixture was allowed to cool. The mixture was filtered and isopropanol was removed in vacuo to afford the product as a viscous, semi-solid (13 g). $^1$H NMR (300 MHz, DMSO d-6) δ 3.89 (t, 2H), 3.78 (t, 2H), 3.66 (s, 2H), 3.17 (s, 6H), 2.27 (t, 2H), 1.51 (m, 2H), 1.23 (s, 16H), 0.85 (t, 3H).

Example 7

Preparation of Dimethylaminopropyl Cocoate

To a 50 mL conical bottom plastic vial was added ethyl cocoate (10 g, 38.5 mmol), dimethylaminopropanol (4.76 g, 46.2 mmol, 1.2 eq) and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale yellow oil (9.2 g) without further purification. $^1$H NMR (300 MHz, CDCl$_3$) δ 4.10 (t, 2H), 2.30 (m, 4H), 2.21 (s, 6H), 1.78 (t, 2H), 1.60 (m, 2H), 1.24 (s, 16H), 0.86 (t, 3H).

Example 8

Preparation of Dimethylaminopropyl Cocoate Betaine

To a 100 mL round bottom flask with a magnetic stir bar and a condenser was added dimethylaminopropyl cocoate (10 g, 35 mmol), sodium chloroacetate (4.1 g, 35 mmol, 1 eq) and 1,3-propanediol (14.1 g). The reaction mixture was heated at 98° C. for 8 hours. When the reaction was complete by NMR, the mixture was allowed to cool. The mixture was filtered to afford the product as a 50% solution in 1,3-propanediol (27 g). $^1$H NMR (300 MHz, CDCl$_3$) δ 4.16 (t, 2H), 3.92 (t, 2H), 3.67 (t, 2H), 3.28 (s, 6H), 2.34 (q, 2H), 2.10 (t, 2H), 1.60 (m, 2H), 1.26 (s, 16H), 0.88 (t, 3H).

Example 9

Preparation of Dimethylaminopropyl Cocoate Betaine

To a 100 mL round bottom flask with a magnetic stir bar and a condenser was added dimethylaminopropyl cocoate (10 g, 35.3 mmol, 1 eq), sodium chloroacetate (4.11 g, 35.3 mmol, 1 eq) and isopropanol (15 mL). The reaction mixture was heated at reflux for 8 hours. When the reaction was complete by NMR, the mixture was allowed to cool. The mixture was filtered and isopropanol was removed in vacuo to afford the product as a viscous, semi-solid (14 g). $^1$H NMR (300 MHz, CDCl$_3$) δ 4.16 (t, 2H), 3.92 (t, 2H), 3.67 (t, 2H), 3.28 (s, 6H), 2.34 (q, 2H), 2.10 (t, 2H), 1.60 (m, 2H), 1.26 (s, 16H), 0.88 (t, 3H).

Example 10

Preparation of Dimethylamino-2-methylethyl Cocoate

To a 50 mL conical bottom plastic vial was added ethyl cocoate (10 g, 38.5 mmol), dimethylamino-2-methylpropanol (5.95 g, 57.7 mmol, 1.5 eq) and Novozym 435 (400 mg).

A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale yellow oil (7 g) without further purification. $^1$H NMR (300 MHz, CDCl$_3$) δ 5.01 (m, 1H), 2.61 (t, 2H), 2.31 (t, 2H), 2.29 (m, 7H), 1.60 (m, 2H), 1.24 (m, 19H), 0.86 (t, 3H).

Example 11

Preparation of Dimethylamino-2-methylethyl Cocoate Betaine

To a 100 mL round bottom flask with a magnetic stir bar and a condenser was added dimethylamino-2-methylethyl cocoate (5.6 g, 18.8 mmol), sodium chloroacetate (2.18 g, 18.8 mmol, 1 eq) and water (7.8 g). The reaction mixture was heated at 98° C. for 8 hours. The pH was kept basic by the addition of 50% NaOH. When the reaction was complete, the mixture was neutralized with 1 M HCl and allowed to cool. The reaction mixture was filtered to afford the product as a 50% solution in water (14 g). $^1$H NMR (300 MHz, DMSO d-6) δ 4.96 (m, 1H), 3.89 (t, 2H), 3.66 (s, 2H), 3.17 (s, 6H), 2.27 (t, 2H), 1.51 (m, 2H), 1.23 (m, 19H), 0.85 (t, 3H).

Example 12

Preparation of Hydrogenated Coconut Oil Methyl Esters

Hydrogenated coconut oil (C$_6$-C$_{18}$ saturated fatty acid triglyceride) (501 g; 0.767 mol) was combined with methanol (123 g; 3.84 mol; 5 equiv) and 25% sodium methoxide in methanol (25 wt %; 19.90 g; 0.092 mol; 0.12 equiv). The mixture was stirred at ambient temperature for 3 hours to afford 99.4% conversion. The stirring was stopped and the lower glycerol layer was decanted. The top layer was concentrated and the crude product was treated with magnesol and filtered to afford the methyl esters of hydrogenated coconut oil fatty acids (476 g; 91%). $^1$H NMR (300 MHz, CDCl$_3$) δ 3.64 (s, 3H), 2.28 (t, 2H), 1.59 (m, 2H), 1.24 (m, 16H), 0.85 (t, 3H).

Example 13

Preparation of 3-Dimethylaminopropyl Hydrogenated Cocoate

Hydrogenated coconut oil fatty acid methyl esters (100 g; 0.44 mol), 3-dimethylaminopropanol (54.5 g; 0.529 mol; 1.2 equiv), Novozym 435 (17 g), and heptane (45 mL) were combined and heated to 65° C. The heptane azeotrope was utilized to remove methanol by reducing the pressure until the azeotrope distilled overhead into a Dean-Stark trap to return the heptane to the reaction vessel. After 8 h GC analysis indicated 99.2% conversion to the 3-dimethylaminopropyl ester of hydrogenated coconut oil fatty acids. The enzyme was removed by filtration and the filtrate was concentrated to afford 131.6 g (92%) of the product. $^1$H NMR (300 MHz, CDCl$_3$) δ 4.09 (t, 2H), 2.31 (t, 2H), 2.27 (t, 2H); 2.20 (s, 6H); 1.77 (m(5), 2H), 1.59 (m, 2H), 1.26 (m, 16H), 0.85 (t, 3H).

Example 14

Preparation of 3-Dimethylaminopropyl Hydrogenated Cocoate Betaine

Sodium chloroacetate (291 g; 2.5 mol; 1.15 equiv) and sodium bicarbonate (36.5 g; 0.435 mol; 0.2 equiv) were added to a jacketed 3-L reactor with a mechanical stirrer and a condenser. Water (1470 mL) and 3-dimethylaminopropyl hydrogenated cocoate (650 g; 2.17 mol) were added and the mixture was stirred and the jacket was heated at 84° C. After 24 h, HPLC analysis indicated 99.0% conversion to product. The mixture was cooled to ambient temperature and the pH of the mixture was adjusted to 6.75 by the addition of 3 M HCl. The resulting mixture was clarified through a scintered glass funnel to afford 2376 g of a 31.8 wt % (by HPLC) solution of 3-dimethylaminopropyl hydrogenated cocoate betaine in water (97% yield). $^1$H NMR (300 MHz, DMSO-d$_6$) δ 4.03 (t, 2H), 3.59 (s, 2H); 3.45 (m, 2H); 3.07 (s, 6H), 2.28 (t, 2H), 1.97 (m, 2H), 1.49 (m, 2H), 1.22 (m, 16H), 0.83 (t, 3H).

Example 15

Preparation of 3-Dimethylaminopropyl Hydrogenated Stripped Cocoate

Hydrogenated and stripped coconut fatty acids (C$_{10}$-C$_{18}$ saturated fatty acid mixture) (375 g; 1.69 mol), 3-dimethylaminopropanol (209 g; 2.03 mol; 1.2 equiv), Novozym 435 (20 g), and heptane (173 mL) were combined and heated to 65° C. The heptane azeotrope was utilized to remove water by reducing the pressure until the azeotrope distilled overhead into a Dean-Stark trap to return the heptane to the reaction vessel. The reaction was allowed to proceed for 8 h at which point GC analysis indicated 99.6% conversion of the hydrogenated stripped coconut fatty acids to the 3-dimethylaminopropyl esters. The enzyme was removed by filtration and the filtrate was concentrated, and the concentrate was purged with nitrogen overnight at 60° C. to remove excess 3-dimethylaminopropanol, 99% yield. $^1$H NMR (300 MHz, CDCl$_3$) δ 4.10 (t, 2H), 2.33 (t, 2H), 2.28 (t, 2H); 2.20 (s, 6H); 1.79 (m(5), 2H), 1.60 (m, 2H), 1.24 (m, 16H), 0.86 (t, 3H).

Example 16

Preparation of 3-Dimethylaminopropyl Hydrogenated Stripped Cocoate Betaine

Sodium chloroacetate (6.53 g; 56.0 mmol; 1.15 equiv), sodium bicarbonate (0.81 g; 9.6 mmol; 0.2 equiv) and 3-dimethylaminopropyl hydrogenated stripped cocoate (15 g; 48.6 mol) were combined in a 100-mL round bottom flask with 33.8 g of water. The mixture was stirred and heated to at 80° C. for 13 h, at which point HPLC analysis indicated 99.3% conversion to product. The mixture was cooled to ambient temperature and filtered to afford 55.88 g of a 32 wt % (by HPLC) solution of 3-dimethylaminopropyl hydrogenated stripped cocoate betaine in water (99% yield). $^1$H NMR (300 MHz, DMSO-d$_6$) δ 4.03 (t, 2H), 3.58 (s, 2H); 3.10 (s, 6H), 2.27 (t, 2H), 1.96 (m, 2H), 1.49 (m, 2H), 1.22 (m, 16H), 0.83 (t, 3H).

Example 17

Preparation of 3-Dimethylaminopropyl Laurate

Lauric acid (600 g; 3.0 mol), 3-dimethylaminopropanol (371 g; 3.59 mol; 1.2 equiv), Novozym 435 (30 g), and heptane (267 mL) were combined and heated to 65° C. The heptane azeotrope was utilized to remove water by reducing the pressure until the azeotrope distilled overhead into a Dean-Stark trap to return the heptane to the reaction vessel. The reaction was allowed to proceed for 12 h at which point GC analysis indicated 99.3% conversion of lauric acid to to the 3-dimethylaminopropyl ester. The enzyme was removed by filtration and the filtrate was concentrated, and the concentrate was purged with nitrogen overnight at 60° C. to remove excess 3-dimethylaminopropanol. $^1$H NMR (300 MHz, CDCl$_3$) δ 4.09 (t, 2H), 2.32 (t, 2H), 2.27 (t, 2H); 2.20 (s, 6H); 1.78 (m(5), 2H); 1.59 (m, 2H), 1.26 (m, 16H), 0.86 (t, 3H).

Example 18

Preparation of 3-Dimethylaminopropyl Laurate Betaine

Sodium chloroacetate (292 g; 2.5 mol; 1.1 equiv) and sodium bicarbonate (38.3 g; 0.455 mol; 0.2 equiv) were added to a jacketed 3-L reactor with a mechanical stirrer and a condenser. Water (219 mL), isopropanol (876 mL), and 3-dimethylaminopropyl laurate (650 g; 2.28 mol) were added and the mixture was stirred and the jacket was heated at 81° C. overnight, at which point HPLC analysis indicated 99.6% conversion to product. The mixture was cooled to ambient temperature and 876 mL of isopropanol was added to afford a precipitate. The mixture was filtered and the filtrate was concentrated at reduced pressure. Water (1000 mL) was added, and the mixture was heated to 80° C. with a headspace nitrogen purge with periodic addition of water to remove residual isopropanol. Once the isopropanol had been evaporated ($^1$H NMR analysis), the mixture was cooled to ambient temperature and the pH was adjusted to 6.75 by the addition of 3 M HCl. The resulting mixture was clarified through a scintered glass funnel to afford 2100 g of a 33.0 wt % (by wt % $^1$H NMR) solution of 3-dimethylaminopropyl laurate betaine in water (89% yield). $^1$H NMR (300 MHz, DMSO-d$_6$) δ 4.03 (t, 2H), 3.58 (s, 2H); 3.10 (s, 6H), 2.27 (t, 2H), 1.96 (m, 2H), 1.49 (m, 2H), 1.22 (m, 16H), 0.83 (t, 3H).

Example 19

Preparation of 3-Dimethylaminopropyl Myristate

Myristic acid (10 g; 43.8 mmol), 3-dimethylaminopropanol (5.87 g; 56.9 mmol; 1.3 equiv), and Novozym 435 (2 g) were combined and heated to 65° C. with nitrogen sparging at 100 mL/min. After 12 h, GC analysis indicated 93.7% conversion of myrstic acid to the ester. The enzyme was removed by filtration and the filter cake was washed with heptane. The filtrate was washed with 1:1 methanol:10% aqueous potassium carbonate (30 mL), then with 5% sodium bicarbonate (15 mL), dried with sodium sulfate, and concentrated to afford 12.09 g (88%) of 3-dimethylaminopropyl myristate. $^1$H NMR (300 MHz, CDCl$_3$) δ 4.11 (t, 2H), 2.33 (t, 2H), 2.29 (t, 2H); 2.22 (s, 6H); 1.79 (m(5), 2H); 1.61 (m, 2H), 1.25 (m, 20H), 0.88 (t, 3H).

Example 20

Preparation of 3-Dimethylaminopropyl Myristate Betaine

3-Dimethylaminopropyl myristate (5.0; g; 15.95 mmol), sodium chloroacetate (2.04 g; 17.54 mmol; 1.1 equiv) and sodium bicarbonate (268 mg; 3.19 mol; 0.2 equiv) were added to a 100-mL round bottom flask. Water (5 mL) and isopropanol (5 mL) were added, and the mixture was stirred and heated to 80° C. for 16 h, at which point HPLC analysis indicated 99.1% conversion. The mixture was cooled to ambient temperature to afford a total solution weight of 15.18 g, indicating approximately 37 wt % 3-dimethylaminopropyl myristate betaine in isopropanol/water. $^1$H NMR (300 MHz, DMSO-d$_6$) δ 4.02 (t, 2H), 3.59 (s, 2H); 3.08 (s, 6H), 2.26 (t, 2H), 1.95 (m, 2H), 1.47 (m, 2H), 1.22 (m, 20H), 0.81 (t, 3H).

Example 21

Preparation of 3-Dimethylaminopropyl Palmitate

Methyl palmitate (10 g; 37.0 mol), 3-dimethylaminopropanol (4.96 g; 48.1 mol; 1.3 equiv), and Novozym 435 (2 g) were combined and heated to 65° C. with nitrogen sparging at 100 mL/min. After 12 h, 98.9% conversion of methyl palmitate to 3-dimethylaminopropyl palmitate was observed along with a little palmitic acid according to GC analysis. The enzyme was removed by filtration and the filter cake was washed with heptane. The filtrate was washed with 1:1 methanol:10% aqueous potassium carbonate (30 mL), then with 5% sodium bicarbonate (15 mL), dried with sodium sulfate, and concentrated to afford 10.00 g (79%) of 3-dimethylaminopropyl palmitate. $^1$H NMR (300 MHz, CDCl$_3$) δ 4.11 (t, 2H), 2.33 (t, 2H), 2.29 (t, 2H); 2.22 (s, 6H); 1.80 (m(5), 2H); 1.61 (m, 2H), 1.25 (m, 24H), 0.88 (t, 3H).

Example 22

Preparation of 3-Dimethylaminopropyl Palmitate Betaine

3-Dimethylaminopropyl palmitate (5.0; g; 14.64 mmol), sodium chloroacetate (1.88 g; 16.1 mmol; 1.1 equiv) and sodium bicarbonate (246 mg; 2.93 mol; 0.2 equiv) were added to a 100-mL round bottom flask. Water (5 mL) and isopropanol (5 mL) were added, and the mixture was stirred and heated to 80° C. for 15 h, at which point HPLC analysis indicated 99.3% conversion. The mixture was cooled to ambient temperature to afford a total solution weight of 13.75 g, indicating approximately 40 wt % 3-dimethylaminopropyl palmitate betaine in isopropanol/water. $^1$H NMR (300 MHz, DMSO-d$_6$) δ 4.02 (t, 2H), 3.59 (s, 2H); 3.09 (s, 6H), 2.26 (t, 2H), 1.95 (m, 2H), 1.48 (m, 2H), 1.20 (m, 24H), 0.81 (t, 3H).

Example 23

Preparation of 3-Dimethylaminopropyl Cocoate

Coconut fatty acid (32.8 g; 0.154 mol), 3-dimethylaminopropanol (18.15 g; 0.176 mol; 1.14 equiv), Novozym 435 (2.62 g), and heptane (15.3 mL) were combined and heated to 50° C. The heptane azeotrope was utilized to remove water by reducing the pressure until the azeotrope distilled overhead into a Dean-Stark trap to return the heptane to the reaction vessel. After 6 h GC analysis indicated 99.0% conversion to the 3-dimethylaminopropyl ester of coconut oil fatty acids. The enzyme was removed by filtration and the filtrate was concentrated to afford 41.64 g (90%) of 3-dimethylaminopropyl cocoate.

Example 24

Preparation of Dimethylaminopropyl Cocoate Betaine

To a 40 mL vial with a magnetic stir bar and a condenser was added 3-dimethylaminopropyl cocoate prepared in example 23 (3 g, 10.0 mmol), sodium chloroacetate (1.35 g, 11.6 mmol, 1.15 eq) and sodium bicarbonate (169 mg; 2.0 mmol; 0.2 equiv). Water (6.82 g) was added and the reaction mixture was heated at 80° C. for 20 hours at which point HPLC analysis indicated 99.0% conversion to the betaine. The reaction mixture was cooled to afford 10.77 g of the product as a 33% solution in water. $^1$H NMR (300 MHz, $CDCl_3$) δ 4.16 (t, 2H), 3.92 (t, 2H), 3.67 (t, 2H), 3.28 (s, 6H), 2.34 (q, 2H), 2.10 (t, 2H), 1.60 (m, 2H), 1.26 (s, 16H), 0.88 (t, 3H). HPLC (150×4.6 mm Zorbax SB-C8 column, 80:20 methanol:water (containing 0.1% trifluoroacetic acid) for 10 min, gradient to 100% methanol over 1 min, held at 100% methanol for 9 min, ELSD detection): $t_R$ (laurate ester) 3.4 min.

Example 25

Preparation of 3-Dimethylaminopropyl Cocoate

Coconut fatty acid (32.8 g; 0.154 mol), 3-dimethylaminopropanol (18.15 g; 0.176 mol; 1.14 equiv), were added to 1080 $cm^2$ of *Candida antarctica* lipase B immobilized on a porous fluoropolymer support as described in US Patent Pub. 20120040395. Heptane (30 mL) was added and the mixture was heated to 50° C. The heptane azeotrope was utilized to remove water by reducing the pressure until the azeotrope distilled overhead into a Dean-Stark trap to return the heptane to the reaction vessel. After 6.5 h GC analysis indicated 99.9% conversion to the 3-dimethylaminopropyl ester of coconut oil fatty acids. The product solution was decanted and the enzyme was washed with heptane. The combined organic solution was concentrated to remove volatiles and afford 43.49 g (94%) of 3-dimethylaminopropyl cocoate.

Example 26

Preparation of Dimethylaminopropyl Cocoate Betaine

To a 40 mL vial with a magnetic stir bar and a condenser was added 3-dimethylaminopropyl cocoate prepared in example 25 (3 g, 10.0 mmol), sodium chloroacetate (1.35 g, 11.6 mmol, 1.15 eq) and sodium bicarbonate (169 mg; 2.0 mmol; 0.2 equiv). Water (6.82 g) was added and the reaction mixture was heated at 80° C. for 20 hours at which point HPLC analysis indicated 99.2% conversion to the betaine. The reaction mixture was cooled to afford 10.97 of the product as a 32% solution in water. $^1$H NMR (300 MHz, $CDCl_3$) δ 4.16 (t, 2H), 3.92 (t, 2H), 3.67 (t, 2H), 3.28 (s, 6H), 2.34 (q, 2H), 2.10 (t, 2H), 1.60 (m, 2H), 1.26 (s, 16H), 0.88 (t, 3H). HPLC (150×4.6 mm Zorbax SB-C8 column, 80:20 methanol:water (containing 0.1% trifluoroacetic acid) for 10 min, gradient to 100% methanol over 1 min, held at 100% methanol for 9 min, ELSD detection): $t_R$ (laurate ester) 3.4 min.

Example 27

Preparation of 3-Dimethylaminopropyl Cocoate

Methyl cocoate (50.0 g; 0.221 mol) and 3-dimethylaminopropanol (28.3 g; 0.274 mol; 1.24 equiv), were added to 150 $cm^2$ of *Candida antarctica* lipase B immobilized on a porous fluoropolymer support as described in US Patent Pub. 20120040395. The mixture was heated to 65° C. and sparged with 100 mL/min of nitrogen to remove the methanol by-product. After 20 h GC analysis indicated 98.7% conversion to the 3-dimethylaminopropyl cocoate.

Example 28

Preparation of Dimethylaminopropyl Myristate

Myristic acid (35.17 g; 0.154 mol), 3-dimethylaminopropanol (18.15 g; 0.176 mol; 1.14 equiv), Novozym 435 (2.62 g), and heptane (15.3 mL) were combined and heated to 50° C. The heptane azeotrope was utilized to remove water by reducing the pressure until the azeotrope distilled overhead into a Dean-Stark trap to return the heptane to the reaction vessel. After 8 h GC analysis indicated 98.5% conversion to 3-dimethylaminopropyl myristate.

Example 29

Preparation of 3-Dimethylaminopropyl Cocoate

Coconut fatty acid (32.8 g; 0.154 mol), 3-dimethylaminopropanol (18.15 g; 0.176 mol; 1.14 equiv), Novozym 435 (2.62 g), were combined and heated to 50° C. Stirring was started and a nitrogen sparge (500 mL/min) was started. After 8 h GC analysis indicated 91.2% conversion to the 3-dimethylaminopropyl ester of coconut oil fatty acids with 3-dimethylaminopropanol still remaining. An additional 0.25 equiv of 3-dimethylaminopropanol (4.0 g; 0.039 mmol) was added and the reaction was continued for an additional 8 h, at which point GC analysis indicated 95.8% conversion. An additional 0.25 equiv of 3-dimethylaminopropanol (4.0 g; 0.039 mmol) was added and the reaction was continued for an additional 6 h, at which point GC analysis indicated 96.7% conversion. The enzyme was removed by filtration and the filtrate was washed with heptane. The combined organic solution was washed with a mixture of 10% aqueous potassium carbonate (25 mL), methanol (25 mL), and water (20 mL). The layers were separated and the top organic layer was concentrated. The residue was dissolved in heptane, dried with sodium sulfate and the volatiles were removed to afford 40.30 g (87%) of 3-dimethylaminopropyl cocoate.

Comparing Examples 28 to 19 and Examples 29 to 23 show the improvement achieved using an azeotroping agent to remove water. In Example 19, without a solvent, conversion of myristic acid to 3-Dimethylaminopropyl Myristate after 12 hours was 93.7%. In Example 28, with a solvent, conversion after 8 hours was 98.5%. Likewise, in Example 29, without a solvent, conversion to 3-Dimethylaminopropyl Cocoate after 8 hours was 91.2% while in Example 23, with solvent, the conversion after 6 hours was 99.0%.

Comparative Example 1

Preparation of Dimethylaminopropyl Cocoamide

To a 50 mL conical bottom plastic vial was added ethyl cocoate (10 g, 38.5 mmol), dimethylaminopropylamine (5.9 g, 57.7 mmol, 1.5 eq) and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material.

The reaction was complete after approximately 24 hours. The reaction mixture was allowed to cool. The Novozym 435 was removed by filtration to afford the product as a pale yellow oil (8.9 g) without further purification. $^1$H NMR (300 MHz, CDCl$_3$) δ 7.02 (s, 1H), 3.28 (m, 2H), 2.32 (m, 2H), 2.18 (s, 6H), 2.10 (t, 2H), 1.59 (m, 4H), 1.21 (s, 16H), 0.84 (t, 3H).

Comparative Example 2

Preparation of Dimethylaminopropyl Cocoamide Betaine

To a 100 mL round bottom flask with a magnetic stir bar and a condenser was added dimethylaminopropyl cocoamide (10 g, 35 mmol), sodium chloroacetate (4.1 g, 35 mmol, 1 eq) and water (14.7 g). The reaction mixture was heated at 98° C. for 8 hours. The pH was kept basic by the addition of 50% NaOH. When the reaction was complete, the mixture was neutralized with 1 M HCl and allowed to cool. The reaction mixture was filtered to afford the product as a 45% solution in water (33 g). $^1$H NMR (300 MHz, DMSO d-6) δ 8.07 (s, 1H), 3.59 (s, 2H), 3.45 (m, 2H), 3.08 (s, 6H), 3.05 (m, 2H), 2.04 (t, 2H), 1.76 (m, 2H), 1.44 (m, 2H), 1.19 (s, 16H), 0.81 (t, 3H).

Comparative Example 3

Preparation of Diethylaminopropyl Cocoamide

To a 50 mL conical bottom plastic vial was added ethyl cocoate (10 g, 38.5 mmol), diethylaminopropylamine (7.52 g, 57.7 mmol, 1.5 eq) and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale yellow oil (11 g) without further purification. $^1$H NMR (300 MHz, CDCl$_3$) δ 7.45 (s, 1H), 3.29 (m, 2H), 2.47 (m, 6H), 2.08 (m, 2H), 1.58 (m, 4H), 1.23 (s, 16H), 0.99 (m, 6H), 0.84 (t, 3H).

Comparative Example 4

Preparation of Diethylaminopropyl Cocoamide Betaine

To a 100 mL round bottom flask with a magnetic stir bar and a condenser was added diethylaminopropyl cocoamide (5 g, 16 mmol), sodium chloroacetate (1.85 g, 16 mmol, 1 eq) and water (5.85 g). The reaction mixture was heated at 98° C. for 8 hours. The pH was kept basic by the addition of 50% NaOH. When the reaction was complete, the mixture was neutralized with 1 M HCl and allowed to cool. The reaction mixture was filtered to afford the product as a 38% solution in water (11 g). $^1$H NMR (300 MHz, DMSO d-6) δ 8.05 (s, 1H), 3.58 (s, 2H), 3.06 (q, 2H), 2.86 (m, 6H), 2.04 (t, 2H), 1.68 (m, 2H), 1.44 (m, 2H), 1.20 (s, 16H), 1.10 (t, 6H), 0.82 (t, 3H).

Comparative Example 5

Preparation of Dimethylaminoethyl Cocoamide

To a 50 mL conical bottom plastic vial was added ethyl cocoate (10 g, 38.5 mmol), dimethylaminoethylamine (5.09 g, 57.7 mmol, 1.5 eq) and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale yellow oil (8.6 g) without further purification. $^1$H NMR (300 MHz, CDCl$_3$) δ 6.25 (s, 1H), 3.25 (m, 2H), 2.34 (t, 2H), 2.16 (s, 6H), 2.10 (t, 2H), 1.54 (m, 2H), 1.18 (s, 16H), 0.80 (t, 3H).

Comparative Example 6

Preparation of Dimethylaminoethyl Cocoamide Betaine

To a 100 mL round bottom flask with a magnetic stir bar and a condenser was added dimethylaminoethyl cocoamide (8 g, 28.3 mmol), sodium chloroacetate (3.3 g, 28.3 mmol, 1 eq) and water (11 g). The reaction mixture was heated at 98° C. for 8 hours. The pH was kept basic by the addition of 50% NaOH. When the reaction was complete, the mixture was neutralized with 1 M HCl and allowed to cool. The reaction mixture was filtered to afford the product as a 50% solution in water (21 g). $^1$H NMR (300 MHz, DMSO d-6) δ 8.33 (t, 1H), 3.65 (s, 2H), 3.61 (m, 2H), 3.42 (q, 2H), 3.14 (s, 6H), 2.06 (t, 2H), 1.45 (m, 2H), 1.20 (s, 16H), 0.83 (t, 3H).

Comparative Example 7

Preparation of Diethylaminoethyl Cocoamide

To a 50 mL conical bottom plastic vial was added ethyl cocoate (10 g, 38.5 mmol), diethylaminoethylamine (6.71 g, 57.7 mmol, 1.5 eq) and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale yellow oil (10.2 g) without further purification. $^1$H NMR (300 MHz, CDCl$_3$) δ 6.21 (s, 1H), 3.32 (m, 2H), 2.56 (m, 6H), 2.21 (m, 2H), 1.65 (m, 2H), 1.29 (s, 16H), 1.04 (m, 6H), 0.92 (t, 3H).

Comparative Example 8

Preparation of Diethylaminoethyl Cocoamide Betaine

To a 100 mL round bottom flask with a magnetic stir bar and a condenser was added diethylaminoethyl cocoamide (5 g, 16.7 mmol), sodium chloroacetate (1.94 g, 16.7 mmol, 1 eq) and water (14.7 g). The reaction mixture was heated at 98° C. for 8 hours. The pH was kept basic by the addition of 50% NaOH. When the reaction was complete, the mixture was neutralized with 1 M HCl and allowed to cool. The reaction mixture was filtered to afford the product as a 38% solution in water (18 g). $^1$H NMR (300 MHz, DMSO d-6)

δ 8.01 (s, 1H), 3.54 (s, 2H), 3.20 (q, 2H), 2.70 (m, 6H), 2.04 (t, 2H), 1.45 (t, 2H), 1.21 (s, 16H), 1.03 (t, 6H), 0.83 (t, 3H).

Comparative Example 9

Preparation of Dimethylaminopropyl Cocoate (Transesterification)

To a 100 mL flask fitted with a distillation head and condenser was added methyl cocoate (10 g, 0.0467 mol) and dimethylaminopropanol (5.77 g, 0.0561 mol, 1.2 eq). To the mixture was added stannous oxalate (0.103 g, 1 mol %). The flask was heated to 100° C. slowly over 1 hour. Over several hours the temperature was increased to 130° C. The reaction was monitored by GC/MS. Methanol was collected in the receiver (ca. 1 mL). The reaction was allowed to cool to room temperature. The mixture was filtered to afford the product as a golden oil (10 g). $^1$H NMR (300 MHz, CDCl$_3$) δ 7.02 (s, 1H), 3.28 (m, 2H), 2.32 (m, 2H), 2.18 (s, 6H), 2.10 (t, 2H), 1.59 (m, 2H), 1.21 (s, 16H), 0.84 (t, 3H).

Comparative Example 10

Preparation of Coconut Fatty Acid

To a 2 L flask was added coconut oil (100 g), methanol (435 mL) and water (307 mL). To this mixture was added 45% potassium hydroxide (88 g). The solution was heated at 45° C. overnight. The reaction was monitored by GC/MS. When the reaction was complete, the mixture was allowed to come to room temperature. To the flask was added methanol (275 mL) and heptane (200 mL). The mixture was stirred and transferred to a separatory funnel. The aqueous layer was returned to the 2 L flask. The organic layer was discarded. To the flask was added water (50 mL). The pH was brought to 1 with the addition of concentrated HCl (ca. 70 mL). The mixture was stirred well and transferred to a separatory funnel. The aqueous layer was removed. The organic layer was dried over MgSO$_4$ and concentrated in vacuo to afford the product as a yellow oil (80 g). $^1$H NMR (300 MHz, CDCl$_3$) δ 11.68 (s, 1H), 2.36 (t, 2H), 1.65 (m, 2H), 1.28 (s, 16H), 0.90 (t, 3H).

Comparative Example 11

Preparation of Dimethylaminopropyl Cocoate (Direct Esterification)

To a 100 mL flask fitted with a distillation head and condenser was added coconut fatty acid (10 g, 0.05 mol,) and dimethylaminopropanol (6.18 g, 0.06 mol, 1.2 eq). The flask was heated to 40° C. (under nitrogen) to melt the fatty acid. To the molten mixture was added stannous oxalate (0.103 g, 1 mol %). The flask was heated to 100° C. slowly over 1 hour. Over several hours the temperature was increased to 150° C. The reaction was monitored by GC/MS. Water was collected in the receiver (ca. 1 mL). The reaction mixture was allowed to cool to room temperature. The mixture was diluted with diethyl ether and washed with saturated sodium bicarbonate solution. The organic layer was dried and concentrated in vacuo to afford the product as a yellow oil (2.6 g). $^1$H NMR (300 MHz, CDCl$_3$) δ 7.02 (s, 1H), 3.28 (m, 2H), 2.32 (m, 2H), 2.18 (s, 6H), 2.10 (t, 2H), 1.59 (m, 2H), 1.21 (s, 16H), 0.84 (t, 3H).

Comparative Example 28

Preparation of Dimethylaminoethyl Laurate

Lauric acid (4.66 g; 23.3 mol), dimethylaminoethanol (1.04 g, 11.6 mmol; 0.5 equiv) and *Candida antarctica* lipase B immobilized on an acrylic resin particle (230 mg) (made in the laboratory whereas in other examples purchased Novozym 435 was used) were combined and heated to 65° C. with a nitrogen sparge to remove the water byproduct. At 2 h, 4 h, and 6 h each an additional 0.50 equiv of dimethylaminoethanol (0.52 g; 5.8 mmol) was added, to afford a total of 2.0 equivalents of dimethylaminoethanol. The reaction was allowed to proceed for a total of 23 h at which point GC analysis indicated 84.9% conversion of lauric acid to the dimethylaminoethyl ester. An additional 0.5 equiv of dimethylaminoethanol was added (0.52 g; 5.8 mmol) and heating was continued. After 5 additional hours (total 29 h) the conversion was 85.8%, indicating that the reaction had stalled.

Comparative Example 12 illustrates a conversion 85.8% after a total of 29 hours when chemical moiety A of formula 1 has only 2 carbon atoms.

The invention has been described in detail with particular reference to preferred embodiments thereof, but it will be understood that variations and modifications can be effected within the spirit and scope of the invention.

We claim:

1. A method for the preparation of a betaine represented by general formula 1,

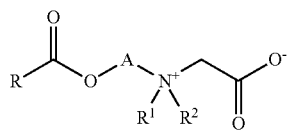

comprising:

a) producing an ester of formula 2:

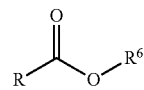

wherein R is selected from the group consisting of C$_5$-C$_{17}$ alkyl, C$_5$-C$_{17}$ alkenyl, C$_5$-C$_{17}$ dienyl, C$_5$-C$_{17}$ trienyl, and mixtures thereof; and R$^6$ is a C$_1$-C$_6$ alkyl;

b) reacting a dialkylamino alcohol 3:

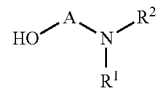

with ester 2 in the presence of an enzyme and an azeotroping solvent to form an intermediate 4:

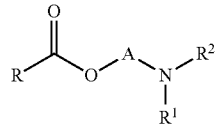

wherein $R^1$ is methyl, $R^2$ is $C_1$-$C_5$ alkyl, and A is $C_3$-$C_{10}$ alkylene; and c) reacting intermediate 4 with sodium chloroacetate to produce a betaine.

2. The method according to claim 1, wherein R is selected from the group consisting of $C_5$-$C_{17}$ alkyl and mixtures thereof, $R^1$ is methyl, $R^2$ is $C_1$-$C_5$ alkyl, and A is $C_3$-$C_8$ alkylene.

3. The method according to claim 1, wherein the ester is produced by solvolysis of non-hydrogenated or hydrogenated triglycerides in the presence of a lower alcohol and a base, acid or enzyme catalyst.

4. The method according to claim 3, wherein the lower alcohol is a $C_1$-$C_4$ alcohol, $R^2$ is methyl, and A is $C_3$-$C_8$ alkylene.

5. The method according to claim 4, wherein the lower alcohol is selected from the group consisting of methanol, ethanol, 1-propanol and 2-propanol, and A is 1,3-propylene.

6. The method according to claim 1, wherein the enzyme is a protease, a lipase, or an esterase.

7. A method for the preparation of a betaine represented by general formula 1,

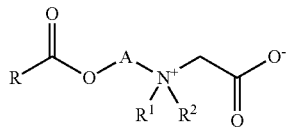

comprising:

a) reacting a carboxylic acid

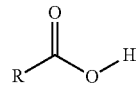

with a dialkylamino alcohol 3:

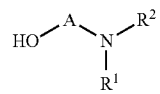

in the presence of an enzyme and an azeotroping solvent to form an intermediate 4:

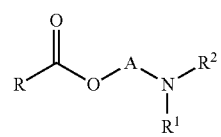

wherein R selected from the group consisting of $C_5$-$C_{17}$ alkyl, $C_5$-$C_{17}$ alkenyl, $C_5$-$C_{17}$ dienyl, $C_5$-$C_{17}$ trienyl, and mixtures thereof; $R^1$ is methyl; $R^2$ is $C_1$-$C_5$ alkyl; and A is $C_3$-$C_{10}$ alkylene; and b) reacting intermediate 4 with sodium chloroacetate to produce a betaine.

8. The method according to claim 7, wherein R is $C_5$-$C_{17}$ alkyl, $R^1$ is methyl, $R^2$ is $C_1$-$C_5$ alkyl, and A is $C_3$-$C_8$ alkylene.

9. The method according to claim 7, wherein $R^2$ is methyl, and A is $C_3$-$C_8$ alkylene.

10. The method according to claim 9, wherein A is 1,3-propylene.

11. The method according to claim 7, wherein the enzyme is a protease, a lipase, or an esterase.

12. The method according to claim 1, wherein the azeotroping solvent comprises heptane.

13. The method according to claim 7, wherein the azeotroping solvent comprises heptane.

* * * * *